United States Patent [19]

Beck et al.

[11] Patent Number: 5,041,586

[45] Date of Patent: Aug. 20, 1991

[54] METHOD OF PREPARING A SILYPHOSPHATE MIXTURE, SILYPHOSPHATE MIXTURE AND ITS USE IN STABILIZING METAL SILANOLATES IN SILOXANE POLYMERS

[75] Inventors: James A. Beck; Peter Lamont, both of Midland, Mich.

[73] Assignee: Dow Corning Corporation, Midland, Mich.

[21] Appl. No.: 622,051

[22] Filed: Nov. 29, 1990

[51] Int. Cl.$^5$ ............................................... C07F 7/08
[52] U.S. Cl. ..................................... 556/405; 528/14; 528/23
[58] Field of Search ..................... 556/405; 528/14, 23

[56] References Cited

U.S. PATENT DOCUMENTS

| | | | |
|---|---|---|---|
| 3,019,248 | 1/1962 | Fekete | 556/405 |
| 3,385,822 | 5/1968 | Brown | 556/405 X |
| 4,125,551 | 11/1978 | Peterson | 260/448.2 E |
| 4,177,200 | 12/1979 | Razzano et al. | 260/448.2 N |

FOREIGN PATENT DOCUMENTS 173332  5/1976  Czechoslovakia ........... 556/405 UX

Primary Examiner—Paul F. Shaver
Attorney, Agent, or Firm—Roger H. Borrousch

[57] ABSTRACT

Silylphosphate mixtures are prepared by slowly adding phosphoric acid to hexamethyldisiloxane under reflux while removing the by-produced water and after the phosphoric acid is added, the temperture is increased to from 150° C. to 170° C. to recover the silylphosphate mixture residue. The mixture has from 10 to 30 weight percent of a monosilyl phosphate of the formula $$\{(CH_3)_3SiO\}(HO)_2P=O,$$

65 to 85 weight percent of a disilyl phosphate of the formula $$\{(CH_3)_3SiO\}_2(HO)P=O,$$

and 2 to 7 weight percent of a trisilyl phosphate of the formula $$\{(CH_3)_3SiO\}_3P=O.$$

These silylphosphate mixtures are useful in stabilizing basic polymerization catalyst such as potassium hydroxide or potassium silanolate and can either be used effectively per se or in combination with carbon dioxide.

6 Claims, 1 Drawing Sheet

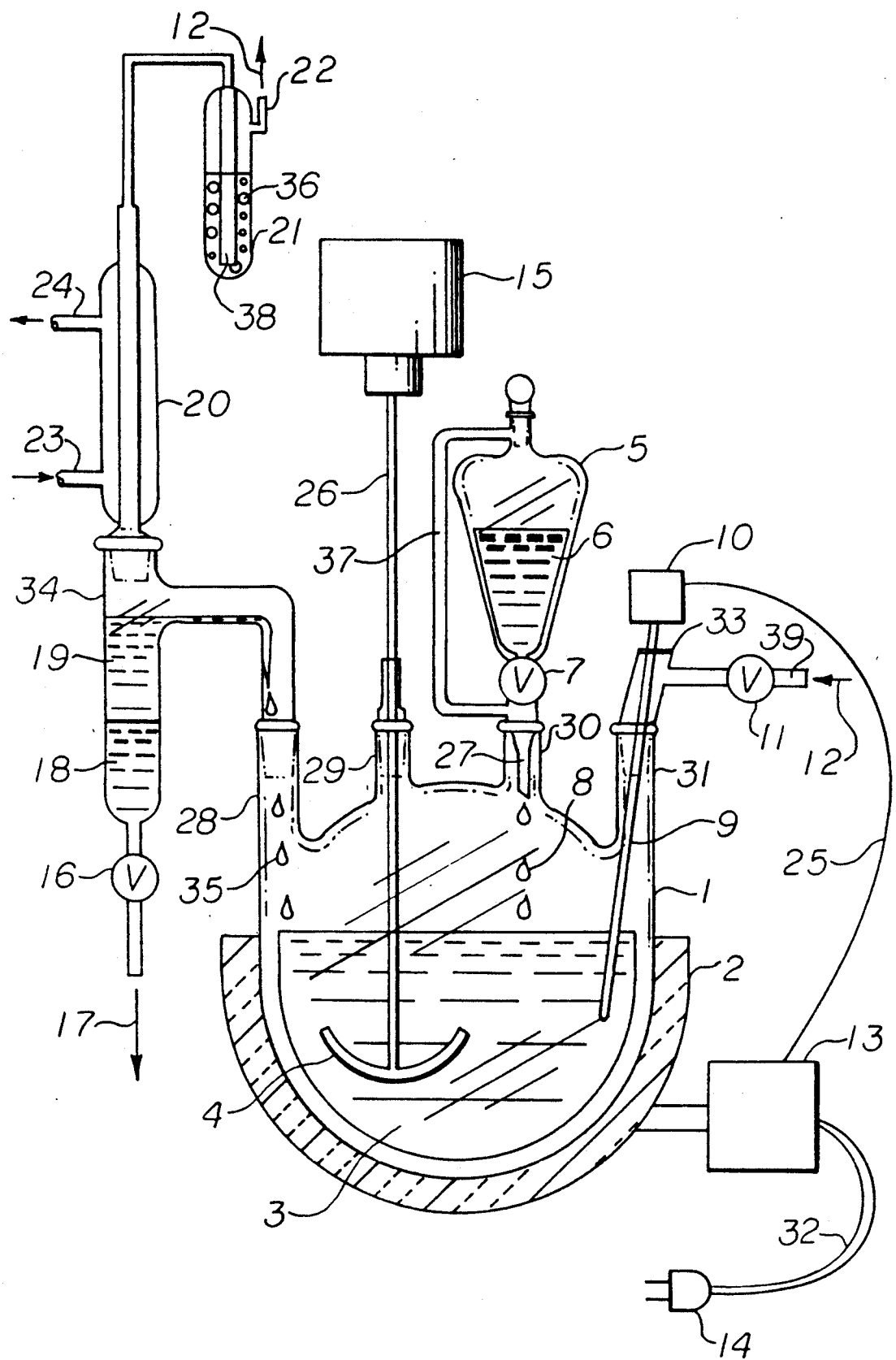

METHOD OF PREPARING A SILYPHOSPHATE MIXTURE, SILYPHOSPHATE MIXTURE AND ITS USE IN STABILIZING METAL SILANOLATES IN SILOXANE POLYMERS

BACKGROUND OF THE INVENTION

1. Field of the Invention

This invention relates to a method of making silylphosphates, to the silylphosphates, and their use in stabilizing alkali metals and alkaline earth metals in polyorganosiloxanes.

2. Background Information

Polydiorganosiloxanes are used in many products, such as various kinds of silicone rubbers and fluids. Many of the products require property stability under high temperature exposure to function properly in their intended utility. Because the polydiorganosiloxanes are most often made by a polymerization process involving strong base equilibration of linear polydiorganosiloxane hydrolyzates or cyclic polydiorganosiloxanes and because this equilibration proceeds via a silicon-oxygen-silicon bond breakage and reformation, the basic polymerization catalyst used must be rendered ineffective if it remains in the final product. The amount of the basic compound is very small and difficult to remove at reasonable cost, so techniques have been developed to reduce the catalyst's harmful effects. The methods of neutralizing the catalyst's activity have varied effectiveness and each method seems to have one or more disadvantages.

Polydiorganosiloxane can be prepared by the well known process of converting low molecular weight linear polydiorganosiloxanes and cyclic polydiorganosiloxanes by heating above 100° C. in the presence of potassium hydroxide or potassium silanolate. Other known alkali metal catalysts for this kind of polymerization, are sodium hydroxide, cesium hydroxide, lithium hydroxide, and their corresponding silanolates or siloxanates. In the case of the cyclic polydiorganosiloxane polymerization, a ring opening reaction takes place with the formation of linear polymers. Most often, such as in the case of polydimethylsiloxane the resulting product of the equilibration reaction is about 85% linear polymer and 15% cyclic polydimethylsiloxanes. The presence of the cyclic siloxanes in products is undesirable because they are of low molecular weight and have a sufficiently high vapor pressure to cause problems during use, such as problems in closed or semiclosed conditions where electrical or electronic equipment is in close proximity with silicone rubber and therefore, these cyclic siloxanes should be removed. The most convenient method of removing these cyclic siloxanes is by heating under reduced pressure, however, if the basic catalyst's activity is not hindered, the distillation process will continuously generate cyclic siloxanes; as they are removed from the linear polydiorganosiloxane product more will be formed because of the reaction's potential to go to equilibrium. Therefore, it is important even in the preparation of the linear polydiorganosiloxanes to stabilize the basic catalyst. Various methods of stabilizing this basic catalyst have been used in the past. Terms, such as neutralizing the catalyst or killing the catalyst have been used in the art with various meanings. The inventors in this application use the term stabilizing the catalyst or stabilization of the catalyst to mean reducing the deleterious activity of metal ions resulting from polymerization reactions, thereby making them ineffective, for the most part, to cause Si-O-Si bond rearrangement and cyclic formation.

One method of neutralizing the basic catalyst is the use of various types of acids. One difficulty with strong acids such as hydrochloric acid or sulfuric acid is that the amount of the acid used must be very carefully controlled because either excess base or excess acid will be detrimental to the final linear polydiorganosiloxanes stability. Both acids and bases are known equilibration catalysts, thus both produce similar results if left in the product. It is known that excess acid will cause degradation of the product similar to the degradation resulting from base such as alkali metal hydroxides. It is difficult to get the base completely neutral using a strong acid and would be very expensive and time consuming. Weak acids have also been used, such as acetic acid, but these acids have a similar problem.

Phosphoric acid, because it is a buffering kind of acid, has the ability to overcome the strong acid problem of neutralizing the basic catalysts used in the preparation of linear polydiorganosiloxane through an equilibration reaction. However, phosphoric acid is not soluble in the linear polydiorganosiloxane or in the cyclic polydiorganosiloxanes and to be an effective catalyst stabilizer it needs to be soluble so that it can get to the alkali metal ions which are often located, when equilibrium is reached, on the terminal silicon atoms of the polydiorganosiloxane product as Si-O-M where M is an alkali metal atom. Solvents are not useful because solvents for the phosphoric acid are not solvents for the siloxanes and solvents for the siloxanes are not solvents for the phosphoric acid. To overcome the difficulty with the insolubility of the phosphoric acid, Razzano et al in U.S. Pat. No. 4,177,200, issued Dec. 4, 1979, found a soluble form of phosphoric acid which could be used to neutralize siloxane mixtures containing alkali metal hydroxides. Razzano et al found that the known silyl phosphates made by reacting phosphoric acid and octylmethylcyclictetrasiloxane and a small amount of hexamethyldisiloxane could be used to neutralize alkali metal hydroxide in siloxanes. However, Razzano et al reported two difficulties with this silyl phosphate. The viscosity of the silyl phosphate was too high, greater than 500 centipoise at 25° C. and this made it difficult to blend with the siloxane equilibration reaction mixture. The other difficulty reported was that the phosphoric acid content of the silyl phosphate could only achieve a maximum of 10 to 15% by weight.

Razzano et al describe a silylphosphate made by reacting a siloxane selected from the class of siloxanes of the formula $(R_3Si)_2O$ and siloxanes of the formula $R_3Si(R_2SiO)_xOSiR_3$ with phosphorous oxyhalogens $POCl_3$ or $POBr_3$ where R is a hydrocarbyl radical free of aliphatic unsaturation and x varies from 1 to 20. Razzano et al also describe a less preferred method for preparing silylphosphates by reacting phosphoric acid with linear siloxanes at temperatures above 150° C. The advantage given for using phosphoric acid in this case is that less of the linear siloxanes are used up in the formation of the silylphosphates. According to Razzano et al, the reaction of phosphoric acid with the siloxanes is difficult and does not take place readily unless temperatures 150° C. to 200° C. are reached. Razzano et al, in a solvent, reacts 1 mole of phosphoric acid with 1.5 moles or more of the siloxane, preferably from 1.5 to 6 moles of the linear siloxanes per mole of phosphoric acid. The by-produced water is distilled off until the reaction is completed taking 1 to 7 hours. The silylphosphate produced are $(R_3SiO)_3P=O$ and $\{R_3SiO(R_2SiO)_x\}_3P=O$ where R and x are defined above. Razzano et al report that because the reaction is carried out with more difficulty and may not proceed to completion there may be some amounts of monosilyl and disilyl substituted phosphate reaction products and the phosphoric acid will be left with one or two hydroxyl groups. The monosilyl and disilyl substituted reaction products may constitute as much as 10% by weight, preferably not more than 5% by weight of the total reaction mixture. The silyl phosphate reaction product consisting mostly of trisilyl substituted phosphates is used to neutralize the equilibration siloxane reaction mixtures having alkali metal hydroxide.

An improved method for preparing silylphosphates from phosphoric acid and linear low molecular weight polysiloxane is described by Petersen in U.S. Pat. No. 4,125,551, issued Nov. 14, 1978. The method taught by Petersen comprises reacting 1 to 30 parts by weight of phosphoric acid with 100 parts by weight of polysiloxane of the formula $R(R_2SiO)_wSiR_3$ where R is a monovalent hydrocarbon radical and w is from 1 to 100 in the presence of 1.2 to 180% by weight of the total composition of a silyl phosphate catalyst in which the phosphoric acid equivalent in the reaction mixture is from 0.36 to 1.80%.

Petersen teaches that the reaction is carried out by placing 5 to 25% of the total phosphoric acid in contact with the polysiloxane and the silyl phosphate catalyst, the mixture is heated and the remaining phosphoric acid is added. The reaction began at 150° C. in most cases and varied upwardly during the reaction period until the final temperature of 175° C. to 196° C. was reached. Petersen found that in all cases where no silyl phosphate catalyst was used in the reaction mixture, the reaction did not initiate for a substantial period of time and then the reaction was violent. Petersen describes the product of the method, as a polymer not having a single composition, but a statistical distribution of a variety of structures and molecular weights about a center point.

The process described by Razzano et al which uses $POCl_3$ or $POBr_3$ to make silylphosphate makes trisilyl phosphates and has the disadvantage of by-producing large amounts of triorganochlorosilane or triorganobromosilane. The method described by Razzano et al which combines phosphoric acid and siloxane to make silylphosphate is violent as described by Petersen who describes the use of a silylphosphate catalyst to make silylphosphate from phosphoric acid and siloxane.

Czechoslovakian Patent No. 173,332, published May 28, 1976, to Dvorak et al teach that making tris(trimethylsilyl)phosphate in high yields from phosphoric acid and hexamethyldisiloxane requires high pressure and high temperature. For example, the reaction is carried out at a pressure of 1 to 10 atmospheres at a temperature of 200° C. for three hours.

SUMMARY OF THE INVENTION

An extensive search for a material useful for stabilizing the basic catalyst used in the preparation of linear polydiorganosiloxanes without the problems associated with the its preparation was conducted by the inventors. Stabilizing is making the catalyst ineffective as an Si-O-Si bond rearrangement catalyst in a practical sense, i.e. the bond rearrangement ability of the metal ion of the catalyst is reduced to a level which produces very small amounts of cyclics when the polydiorganosiloxane is heated. They discovered a new silylphosphate which is a mixture containing very little tris(trimethylsilyl) phosphate and which is prepared by a method which does not react violently, does not require a silylphosphate catalyst to produce a silylphosphate smoothly, and does not require the use of high pressure and an autoclave to produce it.

This invention relates to a method of making a mixture of silylphosphates comprising heating hexamethyldisiloxane to reflux in a closed container equipped with a condenser means, a water trapping means, and a controllable addition means, the hexamethyldisiloxane at reflux existing with a liquid phase and a vapor phase in equilibrium in the closed container, slowly adding phosphoric acid to the hexamethyldisiloxane liquid phase with the controllable addition means while maintaining reflux, the phosphoric acid addition is continued until 40 to 65 parts by weight are added per 100 parts by weight of hexamethyldisiloxane, collecting by-produced water with the water trapping means and removing the collected water at a rate sufficient to keep the water from returning to the liquid phase hexamethyldisiloxane, allowing the temperature of the liquid phase hexamethyldisiloxane to increase to a temperature in the range of 150° C. to 190° C. after the addition of the phosphoric acid is completed, recovering a mixture of silylphosphates.

This invention also relates to a mixture of silylphosphates consisting essentially of 10 to 30 weight percent of a monosilyl phosphate of the formula $$\{(CH_3)_3SiO\}(HO)_2P=O,$$
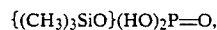

65 to 85 weight percent of a disilyl phosphate of the formula $$\{(CH_3)_3SiO\}_2(HO)P=O,$$
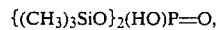

and 2 to 7 weight percent of a trisilyl phosphate of the formula $$\{(CH_3)_3SiO\}_3P=O.$$
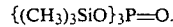

Another embodiment of this invention is using the above described mixture of silylphosphates to stabilize the metal ions in a method of making polydiorganosiloxanes using basic compound having a metal ion comprising combining cyclic or low molecular weight linear polydiorganosiloxanes and the basic compound and heating to polymerize the cyclic polydiorganosiloxane, thereafter stabilizing the metal ion in the resulting polydiorganosiloxane using the mixture of silylphosphates.

Another embodiment of this invention is using, in the above method of stabilizing the metal ion in the polymerization of cyclic or low molecular weight linear polydiorganosiloxanes, a combination of carbon dioxide gas and the mixture of silylphosphate described above.

BRIEF DESCRIPTION OF THE DRAWING

The FIGURE contains a schematic cross section of the apparatus during the manufacture of silylphosphate using phosphoric acid and hexamethyldisiloxane.

LIST OF REFERENCE NUMBERS WITH DEFINITIONS

1: 4-necked round bottom flask
2: heating mantle
3: liquid hexamethyldisiloxane
4: agitator
5: addition flask with pressure equalizer
6: phosphoric acid
7: addition flow control valve
8: phosphoric acid drops dropping into liquid hexamethyldisiloxane
9: thermometer
10: temperature controller-transmitter
11: inert gas flow control valve
12: inert gas flow direction
13: electrical switch with voltage adjustment
14: electrical connector to electrical power source
15: power source for driving agitator 4
16: drain valve
17: discard water from drain valve 16
18: water
19: liquid hexamethyldisiloxane from vapor condenser 20
20: vapor condenser
21: inert gas bubbler
22: inert gas outlet tube
23: cooling water inlet
24: cooling water outlet
25: electrical control wire
26: shaft connecting agitator 4 and power source 15
27: phosphoric acid delivery orifice
28: flask neck
29: flask neck
30: flask neck
31: flask neck
32: electrical cord
33: connecting tube
34: Dean-Stark trap receiver
35: liquid hexamethyldisiloxane flowing back into 4-necked round bottom flask 1
36: inert gas bubbles
37: pressure equalizer line
38: tube
39: inert gas inlet

DESCRIPTION OF THE PREFERRED EMBODIMENTS

The mixture of the silylphosphates of this invention are made by placing liquid hexamethyldisiloxane 3 in a reaction vessel, such as round bottom flask 1, equipped with temperature observation means (thermometer 9), an addition means, such as addition flask 6, agitator 4, and vapor condenser 20. The liquid hexamethyldisiloxane 3 is heated to reflux, about 100° C. When the hexamethyldisiloxane 3 is at reflux, the phosphoric acid 6 is added dropwise, drops 8. The phosphoric acid 6 can be syrupy phosphoric acid, i.e. 85 weight percent phosphoric acid and 15 weight percent water. As soon as the first drops 8 of phosphoric acid are added, water 18 begins to collect in the Dean-Stark trap 34. The reflux is maintained through an interacting combination of thermometer 9, temperature controller 10, connecting wire 25, electrical switch with voltage adjustment 13, and heating mantle 2. The amount of heating is controlled through this arrangement to maintain the reflux at a constant rate. The addition of phosphoric acid 6 will vary depending upon the amounts involved. The phosphoric acid is added at a rate so that the reflux rate is maintained. During the addition of phosphoric acid 6, the liquid hexamethyldisiloxane is stirred with agitator 4. The amount of agitation is not critical but should be sufficient to stir the liquid hexamethyldisiloxane 3 and keep the phosphoric acid from settling to the bottom of flask 1. The hexamethyldisiloxane vapor and the water vapor, either from the phosphoric acid-water mixture or by-produced from reaction of phosphoric acid with hexamethyldisiloxane, condenses in vapor condenser 20, the liquefied hexamethyldisiloxane and water fall into the Dean-Stark trap and separate into liquid hexamethyldisiloxane 19 which flows back into the round bottom flask 1, and water 18 which can be withdrawn at appropriate intervals so that it does not flow back into the liquid hexamethyldisiloxane in flask 1. An inert gas can be introduced, see direction of inert gas 12, through connecting tube 33 with the flow being controlled by valve 11. The inert gas can be dry nitrogen. Prior to the start of the addition of phosphoric acid, the Dean-Stark trap is preferably filled with hexamethyldisiloxane so that the amount of liquid hexamethyldisiloxane in flask 1 remains approximately constant throughout the reaction time.

Phosphoric acid is added slowly so as to maintain the reflux without loosing control, i.e. the temperature is maintained about 100° C. The amount of phosphoric acid added is sufficient to preferably provide from 40 to 65 parts by weight per 100 parts by weight of hexamethyldisiloxane. After the addition of the phosphoric acid is completed, the temperature of the reaction mixture, the material in flask 1, is allowed to increase to a temperature of from about 150° C. to 190° C., preferably about 165° C. During the period of time when the temperature of the reaction mixture is increasing to a temperature of from 150° C. to 190° C., the unreacted hexamethyldisiloxane is preferably removed. This can be done through the Dean-Stark trap 34 via valve 16. After the unreacted hexamethyldisiloxane is removed, the residue remaining in flask 1 is cooled and if it is to be stored for use at a later time, it is packaged in an airtight package. The mixture of silylphosphates is susceptible to degradation upon exposure to moisture and thus should be stored in a container which will not allow the ingress of moisture. The product of the method of this invention is a mixture of silylphosphates as described above. The mixture of silylphosphates may contain a small amount of an unknown by-product material, such as less than 3 weight percent.

The method of this invention proceeds smoothly, does not require the addition of silylphosphate catalyst, and does not need high pressure or high temperatures. The product is a mixture of silylphosphates which contain less trimethylsiloxy groups which are considered contaminates in linear polydiorganosiloxanes. For example, when polydiorganosiloxanes are stabilized with the mixture of silylphosphates of this invention, the amount of triorganosiloxy units introduced is less than when the tris(trimethylsilyl) phosphate of the prior art is used. Triorganosiloxy groups can introduce such groups into the product being stabilized and thus lower amount of trimethylsilyl groups are desirable.

The mixture of silylphosphates is useful as a stabilizing agent for metal ions. Polydiorganosiloxane can be made by polymerizing cyclic polydiorganosiloxanes usually having on the average from 3 to 6 diorganosiloxane units per molecule with basic compounds such as metal hydroxides, namely potassium hydroxide, sodium hydroxide, lithium hydroxide, cesium hydroxide, calcium hydroxide, and magnesium hydroxide or metal silanolates derived from the same metals, preferably potassium hydroxide or potassium silanolate. This polymerization is an equilibrium reaction and the end product contains a quantity of cyclic polydiorganosiloxanes which, for most purposes, are removed. Removal of these cyclics from the product is usually done by stripping operations under reduced pressure at elevated temperature. Under such conditions cyclics would form as soon as some are removed, because an equilibrium is trying to be maintained and new cyclics are formed by the degradation of the linear polydiorganosiloxane product via Si-O-Si bond rearrangement. To overcome this problem, the metal ion, such as the potassium ion, is made ineffective, such as by stabilizing it. The silylphosphates mixture of this invention is a very effective metal ion stabilizer. The cyclics can be removed from the polymerization product with only very small amounts of new cyclic formation and in some cases without the formation of new cyclics. The polydiorganosiloxane product is therefore stable and the metal ion is essentially ineffective to cause degradation of the polymer chain. The amount of the mixture of silylphosphates useful for stabilizing the metal ions in an equilibrium polydiorganosiloxane product is preferably varied to provide at least one phosphate atom per three metal ions. Preferred amounts are at least one phosphate atom per 1.5 metal ions. Low molecular weight linear hydroxyl endblocked polydiorganosiloxanes which are condensed with basic catalysts can be stabilized with the silylphosphate mixtures of this invention.

A very effective metal ion stabilization agent is a combination of carbon dioxide gas and the mixture of silylphosphates. This combination provides the most stable products under conditions of high temperatures, such as above 100° C.

The following examples are presented for illustrative purposes and should not be construed as limiting this invention which is properly delineated in the claims. In the following examples, "part" or "parts" are "part by weight" and "parts by weight" respectively, viscosities are at 25° C. unless otherwise specified, and Me is methyl radical.

EXAMPLE 1

A silylphosphate mixture was prepared in an apparatus as described by the drawing by placing 280 grams of hexamethyldisiloxane in flask 1 with the Dean-Stark trap 34 filed with hexamethyldisiloxane. Flask 1 was heated to start the hexamethyldisiloxane to reflux, about 100° C., then syrupy phosphoric acid (85 weight percent acid with 15 weight percent water) was added dropwise from addition flask 5 through delivery orifice 27. Water began collecting in the Dean-Stark trap immediately and within 20 minutes 5 cc had collected. After one hour and 20 minutes, the temperature of the liquid hexamethyldisiloxane in flask 1 was 103° C. and the amount of water collected was 13.9 grams. The addition of the syrupy phosphoric acid produced a cloudy mixture at first which cleared producing a single phase in about one hour. In two hours and 5 minutes, 200 grams of the syrupy phosphoric acid was added, the temperature was 106° C. The temperature was then increased to 165° C. in 30 minutes and unreacted hexamethyldisiloxane was removed during that period. The total amount of water collected was 44.5 grams. The residue in flask 1 was single phase and clear like water. 406.7 grams of residue was obtained, a yield of 86.8%. The residue as determined by NMR (neuclear magnetic resonance) was the following mixture: 24.3 weight percent $(Me_3SiO)(OH)_2P=O$, 70.3 weight percent $(Me_3SiO)_2(OH)P=O$, 4.3 weight percent $(Me_3SiO)_3P=O$, and 1.1 weight percent unknown by-product.

Silylphosphate Mixture A 1,000 parts of a mixture of cyclic polydimethylsiloxanes in which the majority of the cyclics have from 3 to 6 dimethylsiloxane units, 15 parts of dimethylvinylsiloxy endblocked polydimethylsiloxane having about six dimethylsiloxane units per molecule, and potassium silanolate in an amount to provide 50 ppm potassium were polymerized by heating at 165° C. for 100 minutes. Then, 1.75 parts of a mixture of 10 weight percent of Silylphosphate Mixture A and 90 weight percent of cyclic polydimethylsiloxanes was added to stabilize the potassium ion. The stabilization time was five minutes. The mixture was then stripped for 10 minutes at 225° C. and then cooled to room temperature. The resulting polydimethylsiloxane was endblocked with dimethylvinylsiloxy units, had a viscosity of 15.3 Pa.s as determined by ASTM D 1084 Method B (Brookfield viscosimeter), had an hydroxyl index of 0.948, and a weight loss after 3 hours at 150° C. of 0.596 weight percent as determined on a 5 g sample.

The hydroxyl index is a value obtained by a method which gives an indication of the activity of SiOH present in polysiloxanes by measuring the viscosity before and after catalyzation under controlled conditions. A numerical value obtained is defined as the Hydroxyl Index (OH,I). The value is not related to any actual OH value and range from 1 down to 0.1 units. A sample of polymer to be tested was brought to 25° C.±1° C. and the viscosity was determined using a Brookfield Viscometer with a No. 7 spindle at 50 rpm. The value obtained was recorded as "A". A mixture was prepared by mixing the following ingredients to give a yield of about 500 grams: 100 parts of the polymer, 0.90 part of dibutyltindilaurate, and 0.18 part of trimethylsiloxy endblocked poly(methylhydrogensiloxane) having about 0.7 weight percent silicon-bonded hydrogen atoms. The mixture was heated to 150° C.±1° C. for 1 hour±1 minute. The mixture was then cooled to 25° C.±1° C. and then the viscosity was measured and recorded as "B". The hydroxyl index (OH,I) was calculated to three decimals using the following formula OH,I=A/B.

EXAMPLE 2

A silylphosphate mixture was prepared in an apparatus as described by the drawing by placing 1710 grams of hexamethyldisiloxane in flask 1 with the Dean-Stark trap 34 filed with hexamethyldisiloxane. Flask 1 was heated to start the hexamethyldisiloxane to reflux, about 100° C, then syrupy phosphoric acid was added dropwise from addition flask 5 through delivery orifice 27 at a rate of about 1.25 ml per minute. Water began collecting in the Dean-Stark trap immediately and within 2 hours, 45 grams had collected and the temperature of the liquid hexamethyldisiloxane was 92° C. After 4 hours and 15 minutes, the temperature of the liquid hexamethyldisiloxane in flask 1 was 92° C. and the amount of water collected was 109.14 grams. In 7 hours, 1039 grams of the syrupy phosphoric acid was added, the temperature was 98° C. Increasing the temperature began and within another 30 minutes, the temperature increase to 108° C. and 270 grams of water was removed during that period. The temperature increased to 160° C. in one hour and 30 minutes and unreacted hexamethyldisiloxane was removed. The total amount of water collected was 297.5 grams. The residue in flask 1 was single phase and clear like water. 2151 grams of residue was obtained. The residue as determined by NMR was the following mixture: 20.1 weight percent $(Me_3SiO)(OH)_2P=O$, 72.7 weight percent $(Me_3SiO)_2(OH)P=O$, 6.2 weight percent $(Me_3SiO)_3P=O$, and 1.0 weight percent unknown by-product. (Silylphosphate Mixture B).

Another silylphosphate mixture was prepared as described in this example where the residue as determined by NMR was the following mixture: 22.8 weight percent $(Me_3SiO)(OH)_2P=O$, 70.4 weight percent $(Me_3SiO)_2(OH)P=O$, 5.6 weight percent $(Me_3SiO)_3P=O$, and 1.2 weight percent unknown by-product. (Silylphosphate Mixture C).

EXAMPLE 3

A silylphosphate mixture was prepared in an apparatus as described by the drawing by placing 210 grams of hexamethyldisiloxane in flask 1 with the Dean-Stark trap 34 filed with hexamethyldisiloxane. Flask 1 was heated to start the hexamethyldisiloxane refluxing, about 100° C., then syrupy phosphoric acid was added dropwise from addition flask 5 through delivery orifice 27. Water began collecting in the Dean-Stark trap immediately. The total amount of water collected was 29.45 grams. 100 grams of the syrupy phosphoric acid was added, the temperature was then increased to 190° C. and unreacted hexamethyldisiloxane was removed during that period. The residue as determined by NMR was the following mixture: 14.6 weight percent $(Me_3SiO)(OH)_2P=O$, 79.5 weight percent $(Me_3SiO)_2(OH)P=O$, and 5.9 weight percent $(Me_3SiO)_3P=O$. (Silylphosphate Mixture D).

Five polymerizations (runs) were carried out and each one was stabilized by a different technique as described below. In each polymerization 1,000 parts of a mixture of cyclic polydimethylsiloxanes in which the majority of the cyclics have from 3 to 6 dimethylsiloxane units was heated to 165° C. and then 25 parts of dimethylvinylsiloxy endblocked polydimethylsiloxane having about six dimethylsiloxane units per molecule, and potassium silanolate in an amount to provide 30 ppm potassium were added and then polymerized by heating at 165° C. to 185° C. for 60 minutes. Then, in Run 1, carbon dioxide was used to stabilize the potassium ion (comparative example). In Run 2, a mixture of 8.7 parts of trimethylchlorosilane in 91.3 parts of cyclic polydimethylsiloxanes was added to the polymerization product in an amount to provide one chlorine atom per one potassium ion (comparative example). In Run 3, a mixture of 4.8 parts of acetic acid in 95.2 parts of cyclic polydimethylsiloxanes was added to the polymerization product in an amount to provide one acetic acid molecule per one potassium ion (comparative example). In Run 4, a mixture of 83.2 parts of cyclic polydimethylsiloxanes and 16.8 parts of a purchased silylphosphate which was a mixture of 7 weight percent $(Me_3SiO)_2(OH)P=O$, 88.7 weight percent $(Me_3SiO)_3P=O$, and 4.3 weight percent $\{(Me_3SiO)_2P=O\}_2O$ was added to provide one phosphorus atom per 1.5 potassium ions (comparative example). In Run 5, a mixture of 87.1 parts of cyclic polydimethylsiloxanes and 12.9 parts of Silylphosphate Mixture D was added to provide one phosphorus atom per 1.5 potassium ions. The stabilization time was five minutes. The mixture was then stripped for 10 minutes at 225° C. and then cooled to room temperature. The resulting polydimethylsiloxane was endblocked with dimethylvinylsiloxy units. Table I shows the results obtained in each run. The yield, viscosity by ASTM D 1084 Method B, hydroxyl index by the method as described above, cyclic generation as described below, decomposition rate as described below, and a weight loss after 3 hours at 150° C. on a 5 g sample were determined and are shown in Table I.

TABLE 1

| PROPERTY | RUN 1 | RUN 2 | RUN 3 | RUN 4 | RUN 5 |
|---|---|---|---|---|---|
| Yield, g | 692 | 900 | 884 | 888 | 890 |
| Viscosity, Pa·s | 1.58 | 2.76 | 2.70 | 3.12 | 3.64 |
| OH Index | 0.86 | 0.69 | 0.85 | 0.83 | 0.84 |
| Weight Loss % | 1.59 | 1.54 | 1.39 | 1.23 | 1.02 |
| Cyclic Generation, %* | 18.4 | −1.65 | 0.41 | −0.8 | −0.74 |
| Decomposition Rate, %/min** | 9.6 | — | — | 0.021 | 0.0952 |

*Cyclic generation was determined by the following formula in which 13.7 was the assumed equilibrium concentration (wt %) of cyclic siloxanes:

Cyclic generation =

$$\left[\left[\frac{[gOH + gYield \times (\% \text{ wt. loss}/100)]}{[gOH + gYield]}\right] - 0.137\right] \times 100$$

**The decomposition rate was determined by isothermal thermogravimetric analysis (TGA) at 300° C. with a helium gas flow of 100 cc/min and the instantaneous derivative of the weight loss vs. time was taken after 30 minutes exposure.

The results of this example showed that the silylphosphates of this invention (Run 5) resulted in a lower hydroxyl index than the polymer stabilized with the carbon dioxide (Run 1), and had a lower weight loss than Runs 1, 2, 3, and 4 resulting in a polydimethylsiloxane which was more stable.

EXAMPLE 4

The following mixture was polymerized, 100 parts of cyclic polydimethylsiloxanes as described in Example 1, 0.172 part of dimethylvinylsiloxy endblocked polydimethylsiloxane as described in Example 1, and 0.337 part of potassium silanolate, about 22 ppm K+ in polymer. The mixture was polymerized at 175° C. for about 2.5 hours producing a gum/cyclic mixture of polydimethylsiloxane with dimethylvinylsiloxy endblocks and then it was stabilized by one of two methods.

The silylphosphate mixture used (Silylphosphate Mixture E) in the following methods was a mixture of Silylphosphate Mixture C and Silylphosphate Mixture D in a 50/50 weight mixture. In the first method, the gum/cyclic mixture was stabilized by adding 0.714 part of the silylphosphate mixture as described in Example 3 which was a mixture of 1.36 weight percent of the Silylphosphate Mixture E in cyclic polydimethylsiloxanes.

In the second method, the gum/cyclic mixture was stabilized by adding 0.714 part of the silylphosphate mixture of Example 3 which was a mixture of 1.36 weight percent of the silylphosphate mixture E in cyclic polydimethylsiloxanes and 0.028 part per hour of carbon dioxide gas.

In each method, the stabilization process took about 10 minutes. Each gum/cyclic mixture was stripped of residual cyclics to a weight loss of 1.65 weight percent which was determined by heating a 5 g sample for 3 hours at 150° C. The plasticity and activity of resulting gum from each stabilization method was determined.

The plasticity of the gum from the first method of stabilization was 48 and the plasticity of the gum from the second method of stabilization was 58. The plasticity of the gum was measured by ASTM D926 and the values reported were in thousands of an inch.

The activity of the gum from the first method of stabilization was 68 and the activity of the gum from the second method of stabilization was 15. The activity of the gum is an indication of the amount of silicon bonded hydroxyl group and the lower the activity number the lower the hydroxyl group content. This example showed that the lowest activity and most stable polydimethylsiloxane was obtained by using a combination of silylphosphate and carbon dioxide.

The activity of a silicone polymer is estimated by measuring the increase in plasticity of the polymer before and after compounding with tetraisopropyl titanate and comparing the ratio obtained with the ratio of a standard polymer. Activities in the range of 0 to 75 can be determined by this method.

A Brabender PLAST-CORD, made by C. W. Brabender Instruments Inc., South Hackensack, New Jersey and equipped with a type 6 mixing head in a room controlled to a temperature of 23° C.±1° C. and 50% ±5% relative humidity was used. A sample of the polymer was placed in this room for one hour before the test was conducted. 42.0±0.1 g of polymer was feed into the mixing chamber of the Brabender at a mixing speed of 15±1 rpm. To the mixing polymer 0.08±0.01 g tetraisopropyltitanate was added and the mixing was continued for 10±0.2 minutes with the lid open. Then two 4.2 g ±0.01 g was removed and allowed to rest for 10 minutes. At the same time, two 4.2 g samples of uncatalyzed polymer were made and allowed to rest for 10 minutes. The plasticity as described above of the four samples were measured in the order as weighed. The average of the two uncatalyzed polymer samples was designated "I" and the average of the two catalyzed polymer samples was designated "F". The activity was calculated by the following formula Activity = $(R-1)100$ where $R = F/I$.

That which is claimed is:

1. A method of making a mixture of silylphosphates comprising
   heating hexamethyldisiloxane to reflux in a closed container equipped with a condenser means, a water trapping means, and a controllable addition means, the hexamethyldisiloxane at reflux existing with a liquid phase and a vapor phase in equilibrium in the closed container,
   slowly adding phosphoric acid to the hexamethyldisiloxane liquid phase with the controllable addition means while maintaining reflux, the phosphoric acid addition is continued until 40 to 65 parts by weight are added per 100 parts by weight of hexamethyldisiloxane,
   collecting by-produced water with the water trapping means and removing the collected water at a rate sufficient to keep the water from returning to the liquid phase hexamethyldisiloxane,
   allowing the temperature of the liquid phase hexamethyldisiloxane to increase to a temperature in the range of from 150° C. to 190° C. after the addition of phosphoric acid is completed,
   recovering a mixture of silylphosphates.

2. The method in accordance with claim 1 in which unreacted hexamethyldisiloxane is removed from the mixture of silylphosphates during the period of time as the temperature is increasing to a temperature of from 150° C. to 190° C.

3. The method in accordance with claim 2 in which the recovered mixture of silylphosphate is cooled and packaged in an airtight container for storage.

4. A mixture of silylphosphates consisting essentially of 10 to 30 weight percent of a monosilyl phosphate of the formula $\{(CH_3)_3SiO\}(HO)_2P=O$, 65 to 85 weight percent of a disilyl phosphate of the formula $\{(CH_3)_3SiO\}_2(HO)P=O$, and 2 to 7 weight percent of a trisilyl phosphate of the formula $\{(CH_3)_3SiO\}_3P=O$.

5. In a method of making polydiorganosiloxanes with a basic compound having a metal ion comprising combining cyclic polydiorganosiloxanes and the basic compound and heating to polymerize the cyclic polydiorganosiloxanes or heating to condense low molecular weight hydroxy endblocked polydiorganosiloxanes, thereafter stabilizing the metal ion in the resulting polydiorganosiloxane using a stabilizing material, the improvement consisting of using as the stabilizing material, a mixture of silylphosphates consisting essentially of 10 to 30 weight percent of a monosilyl phosphate of the formula $\{(CH_3)_3SiO\}(HO)_2P=O$, 65 to 85 weight percent of a disilyl phosphate of the formula $\{(CH_3)_3SiO\}_2(HO)P=O$, and 2 to 7 weight percent of a trisilyl phosphate of the formula $\{(CH_3)_3SiO\}_3P=O$.

6. In a method of making polydiorganosiloxanes with a basic compound having a metal ion comprising combining cyclic polydiorganosiloxanes and the basic compound and heating to polymerize the cyclic polydiorganosiloxanes or heating to condense low molecular weight hydroxyl endblocked linear polydiorganosiloxanes, thereafter stabilizing the metal ion in the resulting polydiorganosiloxane using a stabilizing material, the improvement consisting of using as the stabilizing material, a combination of carbon dioxide gas and a mixture of silylphosphates consisting essentially of 10 to 30 weight percent of a monosilyl phosphate of the formula $\{(CH_3)_3SiO\}(HO)_2P=O$, 65 to 85 weight percent of a disilyl phosphate of the formula $\{(CH_3)_3SiO\}_2(HO)P=O$, and 2 to 7 weight percent of a trisilyl phosphate of the formula $\{(CH_3)_3SiO\}_3P=O$.

* * * * *